United States Patent [19]

Boyer

[11] Patent Number: 4,952,071

[45] Date of Patent: Aug. 28, 1990

[54] THERMOCOUPLE PSYCHROMETER

[75] Inventor: John S. Boyer, Lewes, Del.

[73] Assignee: University of Delaware, Newark, Del.

[21] Appl. No.: 314,945

[22] Filed: Feb. 24, 1989

[51] Int. Cl.$^5$ ........................................... G01R 27/26
[52] U.S. Cl. ....................................... 374/24; 73/338; 324/663
[58] Field of Search ..................... 374/24, 28; 73/338, 73/336.5, 336, 73; 324/61 R, 60 CD

[56] References Cited

U.S. PATENT DOCUMENTS

| | | | |
|---|---|---|---|
| 2,702,471 | 2/1955 | Vonnegut | 73/29 X |
| 3,253,465 | 5/1966 | Miller | 73/338 X |
| 4,129,250 | 12/1978 | Chaikin et al. | 73/338 X |
| 4,203,087 | 5/1980 | Kovac et al. | 73/336.5 X |
| 4,584,522 | 4/1986 | Varela | 73/336.5 X |

OTHER PUBLICATIONS

Boyer et al., *Proc. Nat'l. Academy of Science*, 54:pp. 1044–1051, (1965).
Richards et al., *Science*, 12: pp. 1089–1090, (1958).
Spomer, *Agromony J.*, 66, pp. 456–457, (1974).
Boyer, *Proc. Int'l. Conf. on Measurement of Soil and Plant and Water Status*, 3: pp. 26–30, (1967).
Boyer, *Annual Review of Plant Physiology*, 20: pp. 351–352, (1969).
Boyer, *Science*, 154, No. 3755: pp. 1459–1460, (1966).

*Primary Examiner*—Daniel M. Yasich

[57] ABSTRACT

An apparatus for the determination of the water status of living and nonliving materials capable of measuring the vapor pressure of water in the material at thermodynamic equilibrium by matching a solution of known vapor pressure with that of the water in the material, detected by observing the thermocouple output comprising a plurality of spiral loop thermocouples, a recording means for observing the thermocouple output, switches for connecting the thermocouples to the recording means one at a time using latching relays, a pair of contacts for each relay, each contact comprised of layers of dissimilar metals so that the current flowing under a thermalvoltage at the thermocouple in proceeding through the contacts flows through a sequence of metals across the first contact and an exact reverse sequence of metals across the opposing contact. The thermocouple, switches, and relays are contained in thermal and electrical insulation that, together with the low thermal voltage associated with the relays, minimize thermal voltages in all parts of the circuit except the thermocouple. The thermocouple then is used to hold a solution of known vapor pressure that, when enclosed with the material of interest, can be changed until it matches the vapor pressure of water in the material, whereupon the output of the thermocouple becomes zero, identifying the vapor pressure and thus the chemical potential of water in the material.

5 Claims, 4 Drawing Sheets

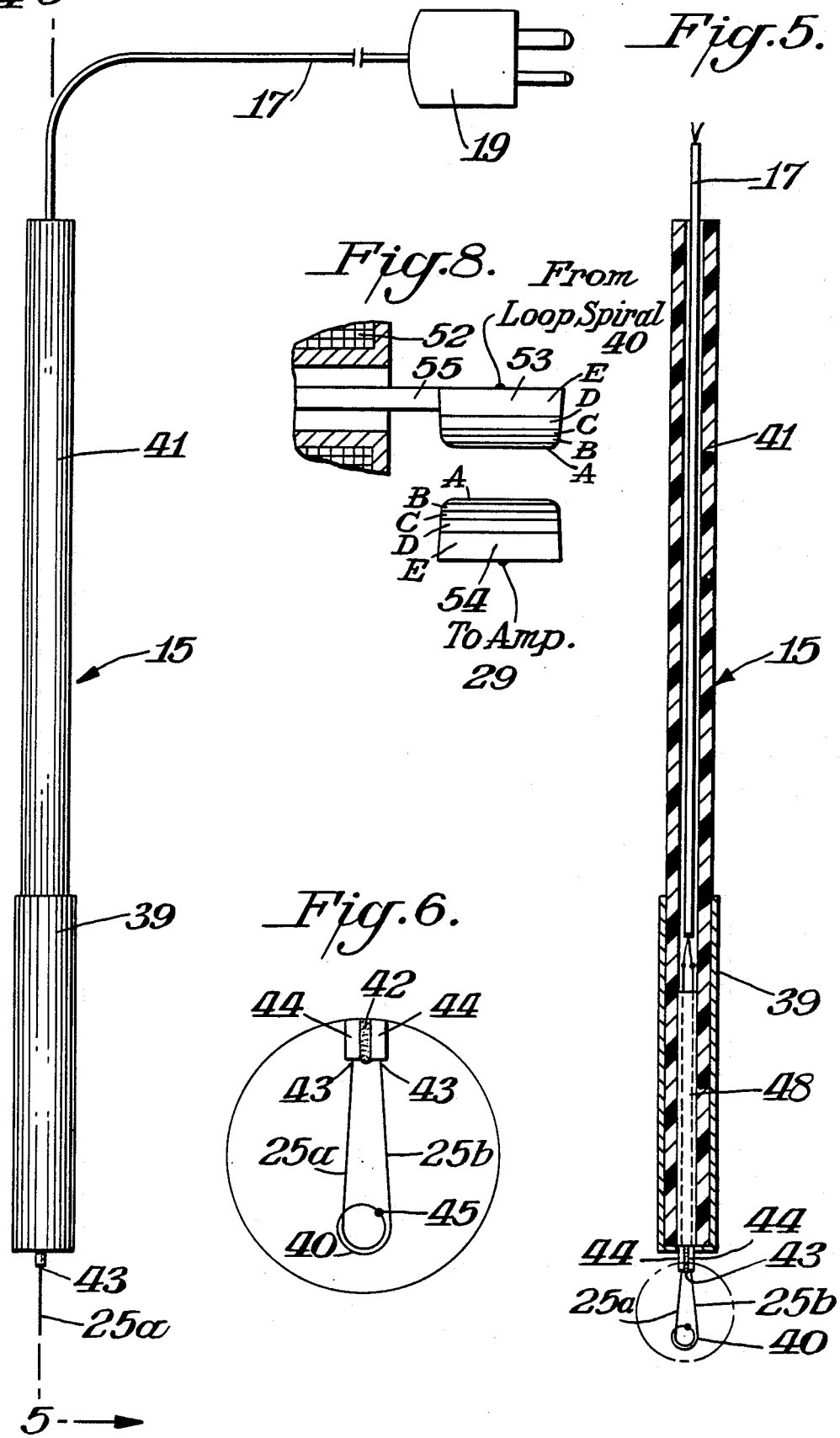

THERMOCOUPLE PSYCHROMETER

This invention relates to the determination of water status in plants and more particularly with isopiestic measurements of water potentials in a thermocouple psychrometer (see below for a description of technique and equipment). More particularly this invention can be applied to the measurement of water potential in living and in nonliving materials.

BACKGROUND OF THE INVENTION

Measurements of the water potential of plant tissue and nonliving samples generally are made with thermocouple psychrometers by enclosing the sample together with a thermocouple in a small container kept at a constant temperature and determining the degree of cooling of the thermocouple as water evaporates from it and is absorbed by the sample. It can be demonstrated that the rate of vapor transfer is proportional to the difference in potential between the thermocouple and sample.

The isopiestic technique is a variant of the above psychrometer technique and uses the psychrometer principle to find a solution which neither loses nor gains water from the sample. The potential of the solution, which is known, is then equal to the potential of the sample. Certain corrections are applied to the measurements and have been shown to be valid; thus allowing the method to give absolute rather than relative measures of water potential; that is, the water potential of a sample having a known potential is the same as the water potential indicated by the instrument. The isopiestic method is the only method developed so far that has been shown to give absolute values of water potential.

To find the solution that neither gains nor loses water from the sample, a solution of known vapor pressure is placed on a thermocouple and sealed together with the sample in the chamber. The thermocouple measures solution temperature and, when the first reading is completed, the solution is replaced with a second solution of different vapor pressure and the reading is repeated. The solution that exchanges no vapor with the sample has the same vapor pressure and thus the same water potential as the sample, i.e., the system is isopiestic and the thermocouple output is zero. In practice, it is not necessary to use a solution that is exactly isopiestic because the output of the thermocouple is linearly proportional to the difference in vapor pressure between each solution and the sample, and the output of the thermocouple can be extrapolated to the isopiestic point.

The advantages of the isopiestic technique are that it is (1) the only technique requiring no calibration,
(2) the only psychrometer method in which the diffusive characteristics of the sample do not affect the determination, and
(3) the only psychrometer method that can measure water potentials higher than −2 bars.

Thus determination is simplified, more accurate, and able to resolve a wider range of water potentials than other techniques.

The measuring of plant water status by the isopiestic technique is disclosed in the article entitled "Isopiestic Technique for Measuring Leaf Water Potentials with a Thermocouple Psychrometer", Proceedings of the National Academy of Sciences, U.S.A., Vol. 54, October, 1965, pp. 1044–1051. The procedure of vapor pressure measurement by liquid on a thermocouple is disclosed in the article entitled "Thermocouple for Vapor Pressure Measurement in Biological and Soil Systems at High Humidity", Science, Vol. 120, Oct. 31, 1958, pp. 1089–1090. The construction and performance of a welded wire, wet loop, thermocouple psychrometer measuring junction are disclosed in an article entitled "Construction of Welded 'Wet Loop' Thermocouple Psychrometer Junctions", Agronomy Journal, Vol. 66, May-June, 1974, pp. 456–457.

Previously known methods of constructing instruments for the isopiestic technique are detrimental to the technique. In particular, thermocouple construction involving difficult soldering creates extraneous thermal activity at the junctions and requires much testing before use. Normal thermal activity of electrical junctions interfere with the isopiestic technique and must be minimized.

Presently there are no switching systems for isopiestic thermocouples capable of automatically switching a plurality of thermocouples that have the low thermal activity that is important to this technique.

It is an object of the present invention to provide an improved thermocouple and an isopiestic technique that (1) has low enough thermal activity at the electrical junctions of the equipment to avoid interference with the test measurements, and (2) has an improved thermocouple that is simple enough to make commercial production feasible.

It is an object of this invention to provide a thermocouple for measuring by the isopiestic technique that supports a substantially more effective object for testing.

It is a further object of this invention to provide a sturdy thermocouple for measuring by the isopiestic technique.

Another object of this invention is providing readings from any of a plurality of thermocouples for measuring by the isopiestic technique by using a switching system for selecting operation of the thermocouples having relays with thermovoltage of the order of ± 5 nanovolts.

SUMMARY OF THE INVENTION

The equipment consists of a thermocouple holding a small droplet of solution (detector), a selector switch, an amplifier, and a readout device.

The thermocouple is made of a pair of dissimilar metals joined with a weld and formed into a spiral loop with the weld disposed inwardly of the loop. The measurement chamber is isothermal to allow ± 0.1 bar accuracy. For this accuracy, the thermocouple output voltages are in the nanovolt range (0.1 bar=approximately 50 nanovolts). As a consequence, the normal thermal activity of electrical junctions that can interfere must be minimized.

The system is protected against thermal gradients and electrical fields. Two methods are employed to avoid interference from thermals in the switch and amplifier system:

(1) the materials are selected to have a minimum thermal activity (small voltage/temperature coefficient) and
(2) temperature gradients are minimized around all nanovolt parts of the system.

Interference from electric fields are prevented by lining the instrument with a thin layer of aluminum and grounding the lining. The invention provides a plurality of thermocouples with a switch system employing relays in which there is low thermal activity. The relays have intrinsically matching junctions having a thermal voltage across the relay contacts in the range of ±.5 nanovolts. In this system the thermal voltages across the electrical junctions are negligible except across the thermocouple.

BRIEF DESCRIPTION OF COMPLETE OPERATION OF INVENTION

The water status of materials such as plants and soils is determined by the water potential measured by the vapor pressure of the water in the material which is detected by placing a solution of known vapor pressure on a thermocouple in a closed chamber with a sample of the material to be analyzed. Solutions of varying vapor pressure are presented and the one neither evaporating nor having water condensing into it is identified. This solution has the same vapor pressure as the sample, i.e., the system is isopiestic. Because the vapor pressure of the solution is known, the vapor pressure of the sample is known. As long as the measurement is isothermal, the water potential alone controls the vapor pressure and thus the water potential is known.

Because the thermocouple outputs are small (a few nanovolts), the method requires that no other thermally-induced voltages be present because they could be confused with that from the thermocouple. This is achieved in the present instrument by making these other thermally active areas isothermal and symmetrical so that their thermal voltages are small and will tend to cancel. A relay switching circuit with symmetrical design allows different thermocouples to be addressed by the amplifier so that several samples can be measured simultaneously in parallel. The thermocouple output is then amplified for readout. Aluminum heat sinks surround the thermocouple, measurement chamber, switching system and amplifier, and these are embedded in an insulated and electrically shielded case. This creates the necessary isothermal, electrically noise-free conditions.

This invention and its objects will become more apparent upon consideration of the following detailed description together with the accompanying drawings.

BRIEF DESCRIPTION OF THE DRAWINGS

FIG. 4 is a side elevational view of a thermocouple assembly of this invention;

FIG. 5 is a sectional view of the thermocouple assembly taken on line 5—5 of FIG. 4 in the direction of the arrows;

FIG. 6 is an enlarged detail of the thermocouple junction tip of the assembly shown in FIG. 5 and 6;

FIG. 8 is a vertical section of a detail of a relay showing the contacts.

DETAILED DESCRIPTION OF A PREFERRED EMBODIMENT

Figure 1:
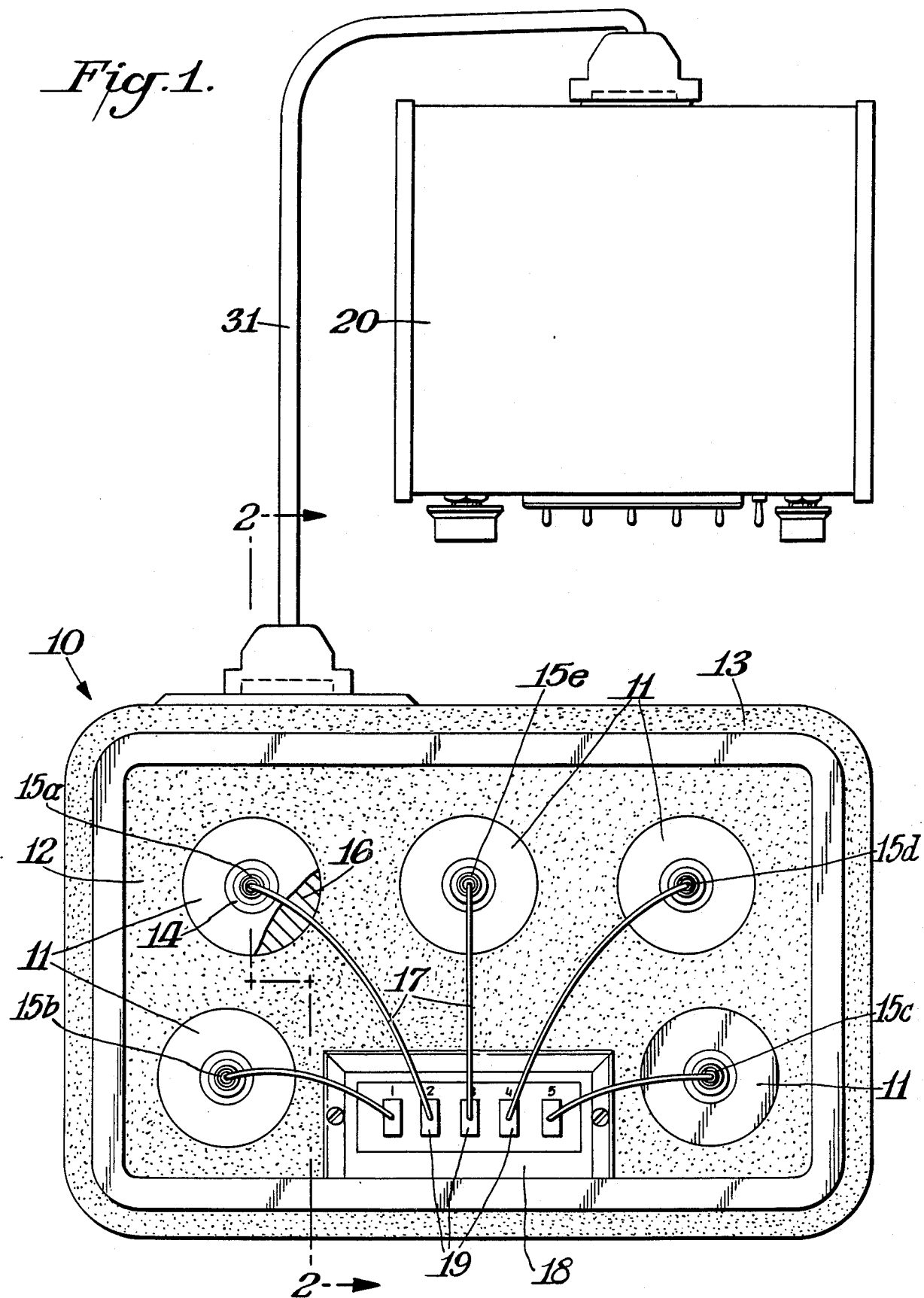
FIG.1 is a top view of the isopiestic psychrometer/-micro-omometer device of this invention.

FIG. 1 is a top plan view of a psychrometer system 10 showing an assembly of sensing units 11 contained in insulation 12 in a chest 13. One of the sensing units 11 shown partly in section (FIG. 2) has an inner heat sink 14 containing a centrally positioned thermocouple assembly 15 and is encompassed by an outer heat sink 16. Each sensing unit 11 contains one of the thermocouple assemblies 15a–15e. Each thermocouple assembly 15 has a lead wire 17 extending to a connector box 18. The thermocouple assembly is illustrated in FIGS. 4, 5 and 8 and is comprised of the lead wire 17, a plastic handle 41, and aluminum heat sink 39, copper wire conductors 44, thermocouple wires 25A and 25B forming a loop spiral 40. A plug 19 on the lead wire 17 mates in the connector box 18. A voltmeter 20 having a liquid crystal display 21 is connected by a cable 31 to the assembly of components in the chest 13 as described more fully below.

Figure 2:
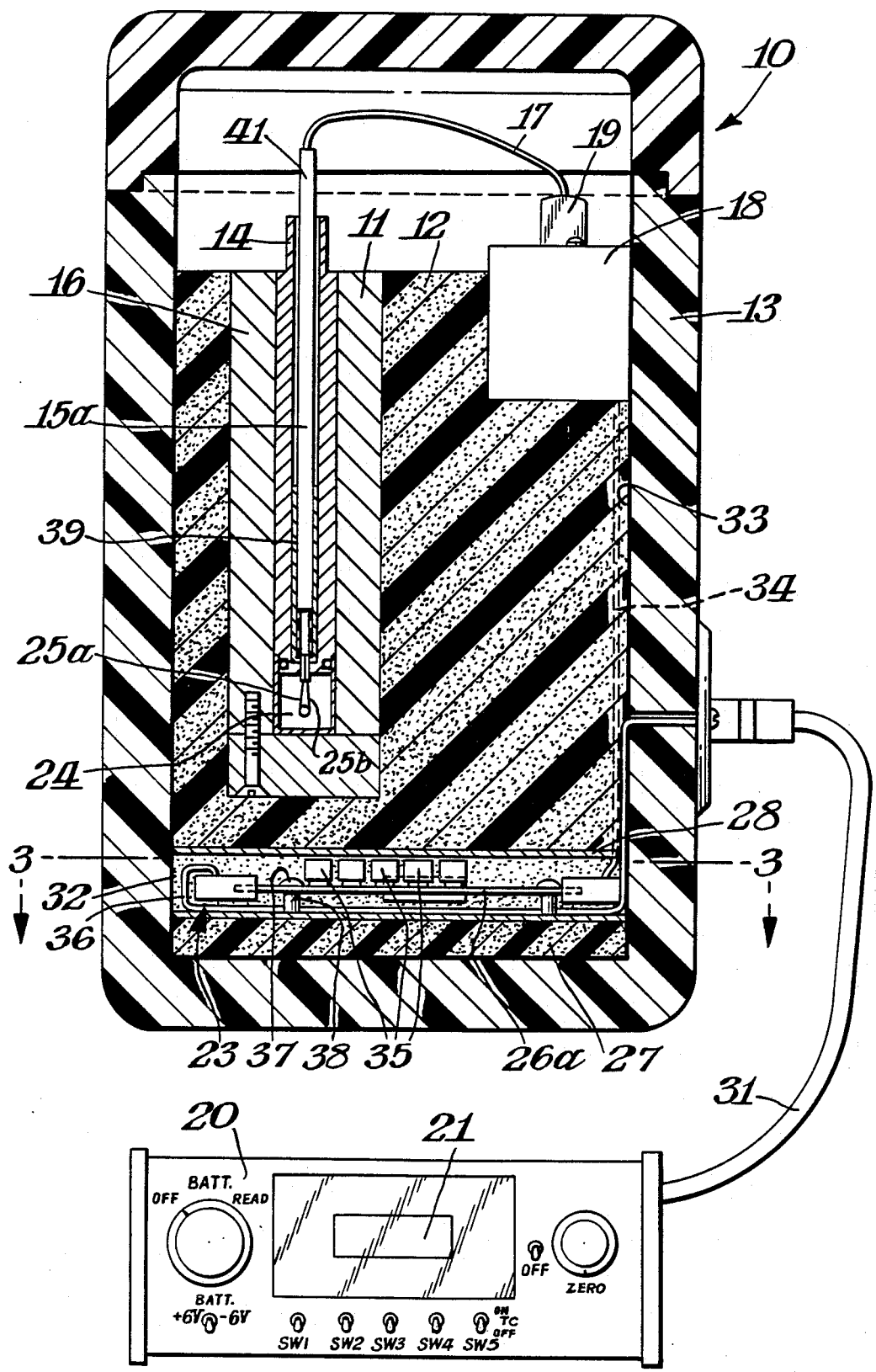
FIG. 2 is a vertical section through the device of FIG. 1 in the direction of the arrows and partly in elevation.

The sectional view of FIG. 2 taken on line 2—2 of FIG. 1 shows the arrangement of components of the psychrometer 10 within the chest 13 and the connection to the voltmeter 20. One of the sensing units 11 is shown in section extending vertically into the insulation 12 for a substantial part of the height of chest 13 and being comprised of the outer heat sink 16 containing the inner heat sink 14, a handle 41 through which the lead wires 17 extend to thin thermocouple wires 25a and 25b in a vapor chamber 24. The two thin wires 25a and 25b are a chromel wire 25a and a constantan wire 25b as explained in greater detail below in relation to FIG. 6.

Figure 3:
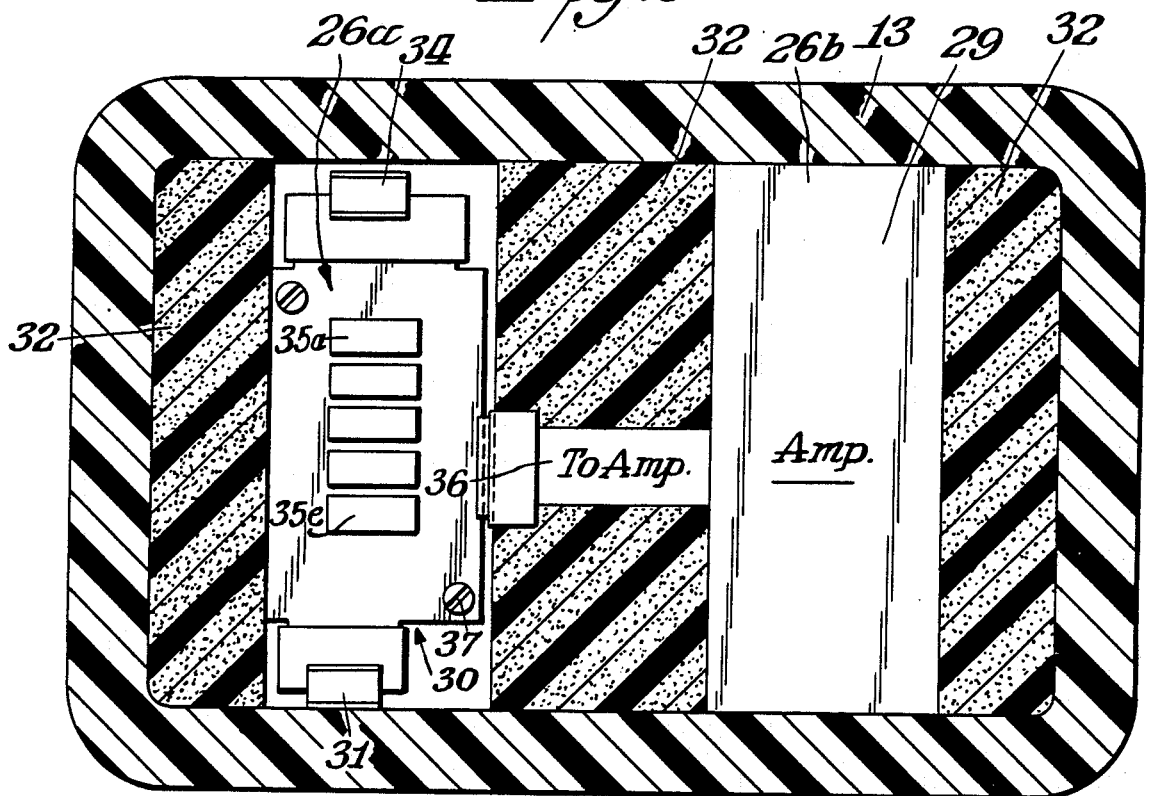
FIG. 3 is a sectional view of the device of this invention substantially on line 3—3 of FIG. 2 in the direction of the arrows showing the switching system.
Figure 7:
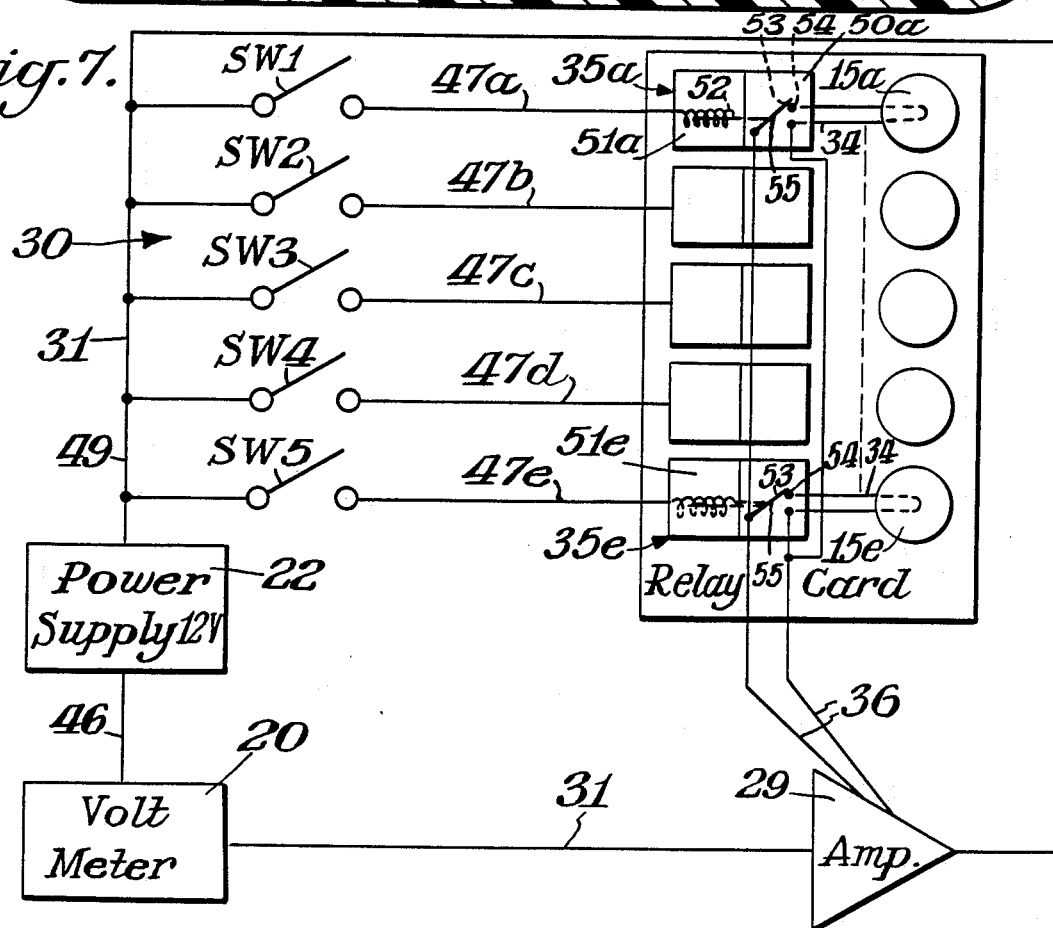
FIG. 7 is a schematic diagram of the circuitry of the device of this invention.

A control unit 23 rests on the interior of the bottom of chest 13 in which two circuit boards 26a and 26b are contained between a pair of lateral extending aluminum plates 27 and 28 as shown in FIG. 3. An amplifier stage 29 is on the board 26b and a switching system 30 are on the board 26a. A suitable amplifier is a modified Decagon NT3. Referring to FIG. 2, a readout cable 31 extending from the amplifier stage 29 passes out of this insulated chest 13 to the digital voltmeter 20 as also shown in FIG. 7. The voltmeter 20 is provided with batteries (not shown) connected to the control unit 23 through cable 31. As shown in FIGS. 2 and 3, insulation separators 32 are positioned at each side of the amplifier stage 29 and switching system 30 and shield the stage 29 and system 30 from thermal gradients and electrical fields. The separators 32 are composed of urethane or styrofoam.

FIG. 2 shows the insulated chest 13 has an aluminum lining 33 suitably provided, such as by aluminum tape. The chest 13 is constructed of insulator material such as styrofoam. This construction provides shielding of the thermocouple assemblies 15 and the amplifier stage 29 and the switching system 30 from thermal gradients and electrical fields.

As indicated above in the device of the present invention, readings from any of the several thermocouples may be obtained on the voltmeter 20 through the operation of the switching system 30 illustrated in the diagram of FIG. 7.

FIG. 3 is substantially a sectional view of the device of this invention taken on line 3—3 of FIG. 2 and illustrating the switching system 30, amplifier stage 29 and separators 32 as seen from above in the chest 13. A cable 34 shown in FIG. 2 connected from the connector box 18 brings the electrical output from the thermocouple assemblies 15 to relays 35. The relays 35 in the system 30 are connected so as to relate a relay 35 to a respective assembly 15. Cable 36 shown in FIGS. 3 and 7 connect contacts side 50a–50e of the relays 35 to the amplifier stage 29, passing through the separator 32, while observed results are conducted to the voltmeter 20 on the readout cable 31. It is to be noted that the lines 34, 36 and 31 connecting the thermocouples 15a–15e, the contact sides 50a–50e and the amplifier 29 to the voltmeter 20 are not connected to the power supply 22.

An end view of the relays 35 on the circuit board 26a is shown in FIG. 2. The relays 35 are soldered to the circuit board 26a which board 26a is in turn mounted on aluminum plate 27 on plastic screws 37 and plastic spacers 38.

In the thermocouple psychrometer of the present invention, vapor pressures are measured in reference to the isopiestic point which is equilibrium where no net condensation or evaporation takes place in the vapor chamber 24. In this psychrometric system, in the circuit containing thermocouple strands 25a and 25b and the respective relays 35a–35e, the isopiestic point calls for an electrical potential of zero. The relay 35 of this invention when in the circuit with dissimilar strands 25a and 25b must at all times have a potential of zero so that the approach to zero at the thermocouple can be detected. As noted below, the construction of the relay 35 contacts is based on a sequence of different metals that is repeated in opposite order on opposing contacts, and any residual thermal voltages cancel each other. Because the relay contact voltage is thus zero, any thermocouple voltage is applied to the amplifier and will appear accurately on the voltmeter 20.

FIG. 3 shows relays 35a–e, one for each of the thermocouple assemblies 15a–e. The selective activation of the relays 35a–e is accomplished through the connection through line 49 to the power supply 22 as shown in FIG. 2.

For illustrative purposes in FIG. 4 a representative thermocouple 15 is shown having an aluminum heat sink 39 and the thermocouple of strands 25a and 25b formed into the loop spiral 40 to provide a thermocouple measurement junction. The plastic handle 41 has a central passage, as shown in FIG. 5 through which lead wire 17 runs to an electrical plug 19.

FIG. 5 is a sectional view on line 5—5 of FIG. 4 illustrating the electrical lead wire 17 in the representative thermocouple assembly 15. The lead wire 17 runs through the handle 41 to heavy duty copper wire conductors 44 insulated and bedded in epoxy cement in the heat sink 39. The conductors 44 pass through the heat sink 39 and are connected at reference junctions 43 to the thermocouple strands 25a and 25b. As shown in the enlarged detail of FIG. 6 the thermocouple is made of chromel strand 25a and constantan strand 25b joined at weld 45 and fashioned into loop spiral 40. The weld 45 is turned to the inside of the spiral 40. The tight loop spiral 40 may have a diameter of 2mm but can be wound to any diameter that will retain an adequate sample of solution. The spiral is wound so that no part is in contact with any other part. The thermocouple strands 25a and 25b coiled in spiral form are coiled so as to complete at least one and one-half coils. The conductors 44 are held apart and electrically insulated by a spacer 42.

Referring to FIG. 2 it is seen that heat sink 39 of the assembly 15 is mounted in the inner small heat sink 14 and together the assembly 15 and sink 14 are positioned in the outer heat sink 16 to define to define the vapor chamber 24. The assembly 15 can be removed to facilitate replacement of liquid on the loop spiral 40.

FIG. 7 is a general schematic diagram of the circuitry of the psychometer system 10. The relays 35a–35e are illustrated as having contact sides 50a–50e and electromagnet sides 51a–51e. The interconnection between these respective sides is represented by a broken line. The supply 22 provides power to the volt meter 20 through line 46 and to the electromagnet sides 51a–51e through line 49. Switches SW1, SW2, SW3, SW4 and SW5 connect the respective electromagnet sides 51a through 51e to the source of power, supply 22. The thermocouple assemblies 15a through 15e are represented in FIG. 7 associated with the respective contact sides 50a–50e through cable 34. The switches SW1–SW5 control the operation of the respective assemblies 15a–15e by closing the contact or connecting the supply 22 through wires 47a to 47e. The relays 35a–35e when selectively energized by closing of the respective switches SW1–SW5 bring the respective thermocouple assembly 15a–15e into operation.

A balance in the thermocouple electrical circuit can be obtained by having two junctions of dissimilar metals and the flow of the current under thermal voltage in one junction the reverse of the flow in the other junction. It is an object of the present invention to keep the relay which interconnects the thermocouple assembly to the control unit 23 thermally inactive.

In the described embodiment the selective interconnection of the thermocouple assemblies 15a–15e to the control unit 23 to the amplifier 29 and voltmeter 20 is effectuated by the energizing of the electromagnet 52 for the respective relay 35a–35e. As indicated above, the electromagnets 52a–52e receive power upon closing of the respective switch SW1–SW5. This in turn results in closing of contacts 53 and 54 for the selected thermocouple 15. The influence of the electromagnets 52a–52e on the respective contacts 53a–53e and 54a–54e is indicated by dotted lines. The relay 35 of this invention is a latching relay in that with an impulse of some polarity the relay switches momentarily in the opposite sense.

The relays 35a–35e have contacts 53a–53e and 54a–54e which are moved with relation to each other by energizing an armature operating in a magnetic field. 53a–54e are moving contacts and 54a–54e are fixed contacts.

There is low thermal voltage across the contacts.

The contacts are made up of a sequence of different metals in layers, so that the relays have matching junctions in the contacts which match each other in thermal voltage. As this invention provides that the relays are thermally and electrically isolated, the thermal voltage across the relay contacts is in the range of ± 5 nanovolts.

There is a temperature gradient of no more than 0.001 C. across any part of the relay 35.

FIG. 8 illustrates appropriate relay contacts in moving contact 53 and fixed contact 54.

The electromagnetic coil 52 surrounds finger 55 on which the moving contact 53 is mounted. Each contact is made up of five layers A-E. One suitable combination of layers is as follows:

| | Composition | Thickness in mm. |
|---|---|---|
| Layer A | gold-silver alloy | .005 |
| Layer B | silver-nickel alloy | 0.06 |
| Layer C | silver-tin oxide alloy | 0.14–0.2 |

-continued

|  | Composition | Thickness in mm. |
| --- | --- | --- |
| Layer D | silver (minimum 99.8%) | 0.025 |
| Layer E | copper-nickel alloy | base support |

The current from the thermal voltage at the thermocouple loop spiral 40 flowing to the test equipment flows through the contacts 53 and 54 as illustrated in FIG. 8, and flowing first to contact 53 and on actuating contact with contact 54, through contact 54 to the amplifier 29 and subsequently to the voltmeter 20. The current thus on passing through contact 53, flows first into the base E of contact 53 and then successively to layers D, C, B and A of contact 53 and, after crossing the contact 54 and then successively through layers B, C and D to base E of contact 54. Thus the current flow proceeds successively through the layers E, D,C, BA, AB, C, D, E. The symmetry is vitally important in providing the balancing of thermovoltages as the current passes through the actuated relay 35. This in turn is instrumental in providing a balance of zero voltage in the thermocouple circuit and reducing the thermal activity of the circuit extraneous to the measurements made in a sample on the loop spiral 40. In short, the succession of current flow through the layers of the one contact, 53, is the reverse of the succession of flow thorough the layers of the other contact 54.

The loop spiral 40 of the activated assembly 15 is then available for measuring by the isopiestic technique by recording thermal voltage across the junction at weld 45. The detected thermal voltage is carried over cable 36 to the amplifier 29 and the amplified signal transmitted to the voltmeter where it is appropriately displayed, as for example on the liquid crystal display 21. As described above, the measurement of water potential of a subject and of a sample is taken by detecting the thermal voltages across the thermocouple weld 45.

The product of the thermocouple operation is an electrical potential output resulting from the effect of the liquid on the loop spiral 40.

What is claimed is:

1. A system for measuring by the isopiestic technique comprising
   a plurality of thermocouples,
   an observation means operably connectible to said thermocouples to display indicia of thermal voltage produced at said thermocouples,
   a switching system operable to selectively connect individual thermocouples to said observation means,
   said switching system comprising:
   a latch-type relay connectible to each individual thermocouple operable to connect the respective thermocouple to said observation means,
   each latch-type relay comprised of an electromagnet and a pair of contacts having contacting surfaces operated by said electromagnet,
   said contacts comprised of metal layers of dissimilar compositions arranged in a sequence wherein the progression of the layers from the contact surface in each contact is the same,
   so that current flowing through the relay moves through a succession of layers in a first contact and then flows through a reverse succession of layers in a second contact.

2. The system as claimed in claim 1 wherein said thermocouples have two dissimilar metal wires joined in a spiral loop.

3. The system as claimed in claim 2 in which a weld inwardly of the spiral loop joins the dissimilar metal wires.

4. Apparatus for determining water status in material by the isopiestic technique comprising:
   a plurality of thermocouples each having a bimetallic loop spiral,
   each thermocouple having means for electrical connection to a power supply and to recording means responsive to a voltage produced at the loop spiral said connection means including a latch-type relay,
   each relay comprised of an electromagnet and a pair of contacts having contacting surfaces operated by said electromagnet,
   said contacts comprised of metal layers of dissimilar compositions arranged in a sequence wherein the progression of the layers from the contact surface in each contact is the same,
   so that current flowing through the relay moves through a succession of layers in a first contact and then flows through a reverse succession of layers in a second contact.

5. Apparatus for determining water status in material by the isopiestic technique comprising:
   a plurality of thermocouples, each thermocouple consisting of two strands of metal of dissimilar composition coiled in spiral form and joined by a weld positioned in a loop of said coil,
   each thermocouple having means for electrical connection to a power supply and to recording means responsive to a voltage produced at the loop spiral said connection means including a latch-type relay,
   each relay comprised of an electromagnet and a pair of contacts having contacting surfaces operated by said electromagnet,
   said contacts comprised of metal layers of dissimilar compositions arranged in a sequence wherein the progression of the layers from the contact surface in each contact is the same,
   so that current flowing through the relay moves through a succession of layers in a first contact and then flows through a reverse succession of layers in a second contact.

* * * * *